United States Patent [19]

Hallisey

[11] Patent Number: 4,669,457

[45] Date of Patent: Jun. 2, 1987

[54] ORTHOPEDIC BRACE HAVING ELONGATED LIMITING ELEMENT BENDABLE IN ONE DIRECTION ONLY

[76] Inventor: William F. Hallisey, 85 South St., Ware, Mass. 01082

[21] Appl. No.: 753,180

[22] Filed: Jul. 9, 1985

[51] Int. Cl.⁴ .................. A61F 5/01; F16D 1/00; F16F 1/18

[52] U.S. Cl. ................... 128/80 C; 128/80 F; 128/88; 403/220; 403/291; 267/158

[58] Field of Search ............ 128/80 C, 80 F, 80 R, 128/88; 16/225, 226, 363, 362; 267/158, 73, 74; 403/117, 112, 113, 119, 220, 291; 2/22, 24

[56] References Cited

U.S. PATENT DOCUMENTS

| | | | |
|---|---|---|---|
| 977,224 | 11/1910 | Robinson et al. | 403/220 |
| 3,587,572 | 6/1971 | Evans | 128/80 |
| 3,928,872 | 12/1975 | Johnson | 128/80 C |
| 4,013,070 | 3/1977 | Harroff | 128/80 C |
| 4,064,874 | 12/1977 | Valin | 128/80 C |
| 4,115,902 | 9/1978 | Taylor | 128/80 C |
| 4,130,115 | 12/1978 | Taylor | 128/80 C |
| 4,219,892 | 9/1980 | Rigdon | 128/80 C |

FOREIGN PATENT DOCUMENTS 838479  5/1952  Fed. Rep. of Germany .... 128/80 F

Primary Examiner—Edgar S. Burr
Assistant Examiner—Tonya Lamb
Attorney, Agent, or Firm—Norman S. Blodgett; Gerry A. Blodgett

[57] ABSTRACT

Brace for use on a body limb having a joint, wherein a cuff is adapted to be attached to the limb above the joint and a cuff to be attached to the limb below the joint, the two cuffs being joined by a connecting member. The connecting member consists of a main body having a track in which lies a limiting element, the limiting element allowing the main body to be bent one direction only, but not in any other.

10 Claims, 8 Drawing Figures

4,669,457

ORTHOPEDIC BRACE HAVING ELONGATED LIMITING ELEMENT BENDABLE IN ONE DIRECTION ONLY

BACKGROUND OF THE INVENTION

There are many situations in orthopedic and sports medicine where a joint needs to be protected. This is particularly true of the knee joint in the game of football. The knee joint, for example, is capable of pivoting in the rearward direction, but can not be moved forward or sideways of the upper leg without substantial injury to muscles, tendons, and bones. When the knee joint has been subjected to the wrong movement, due to the player being tackled and so on, the knee tends to develop permanent injuries which do not heal between games. Attempts, therefore, have been made to prevent such deleterious movement by developing braces which inhibit that forward or "wrong way" motion, as well as to resist lateral motion of the lower leg relative to the upper leg. These braces are intended not only to protect the leg against being injured in the first place, but also to prevent it from receiving additional injurious articulation in directions that the knee joint is not supposed to move. Braces of this type that have been developed in the past have usually been made of metal having hinges that coincide with the hinge line of the knee. In order to fit one of these very expensive braces properly, a mold of the leg was necessary, making it an expensive and time-consuming process, since it is custom-fitted. Secondly, wearing a hinged brace on each leg as a prophylaxis against adverse trauma is completely unsatisfactory, because the inner aspect of the braces strike each other unless the user runs with his legs apart. Running in this way would be unsatisfactory to an athlete who depends on speed and agility.

The braces developed in the past were prone to slip when sweat was present. Some of the braces are designed to protect against the most common football injury which is a tear of the medial collateral ligament. In such case, there is no protection to the cruciate ligaments, which are the criss-cross band of thick ligaments deep within the knee cavity which prevents hyperextension of the knee, and also prevents instability of the upper femur on the lower tibia platform. This type of injury can be very devastating and the repair requires the most meticulous surgery which is not always succesful. Furthermore, most of the braces of the past have been very heavy which prevents their use with the athlete who is a child or a high school student. These and other difficulties experienced with the prior art devices have been obviated in a novel manner by the present invention.

It is, therefore, an outstanding object of the invention to provide an orthopedic brace which not only protects against tearing of the medial collateral ligament, but also protects against injury to the cruciate ligaments.

Another object of this invention is the provision of a brace which is light in weight and which carries no interfering elements on the inside of the knee that would inhibit running.

A further object of the present invention is the provision of a light-weight brace for protecting the knee joint against injury and which is light enough so that it does not interfere with running.

It is another object of the instant invention to provide a knee joint brace that does not require custom fitting.

A still further object of the invention is the provision of an orthopedic brace which is simple in construction, which is inexpensive to manufacture, and which is capable of a long life of useful service with a minimum of maintenance.

It is a further object of the invention to provide an orthopedic brace for the protection of the knee joint, which may be used by small children, persons of high school age, and by adults as a protective measure in rough sports.

Another object of the invention is the provision of an orthopedic brace that resists bending in the lateral and forward directions, but permits bending in the rearward direction.

With these and other object in view, as will be apparent to those skilled in the art, the invention resides in the combination of parts set forth in the specification and covered by the claims appended hereto.

SUMMARY OF THE INVENTION

In general, the invention consists of an orthopedic brace for use with a body limb, comprising a first cuff for embracing the limb at one side of a joint and a second cuff for embracing the limb at the other side of the joint. An elongated connector, including a main body formed of an elastomer material, connects the two cuffs and is capable of bending in one direction only to allow articulation of the limb, means being provided preventing the main body from bending in any other direction.

More specifically, the elongated main body is formed with a longitudinal track having a transverse stop surface at each end, the track being located at one side of the neutral plane of the main body, the preventing means being an elongated limiting element lying in the track on the said one side of the neutral plane and having ends lying adajacent the said stop surfaces of the track. The main body and the limiting element are bendable from a first normal position (in which the ends of the limiting element are substantially in contact with the stop surfaces) to a second bent position (in which the ends of the limiting element are substantially separated from the stop surfaces).

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
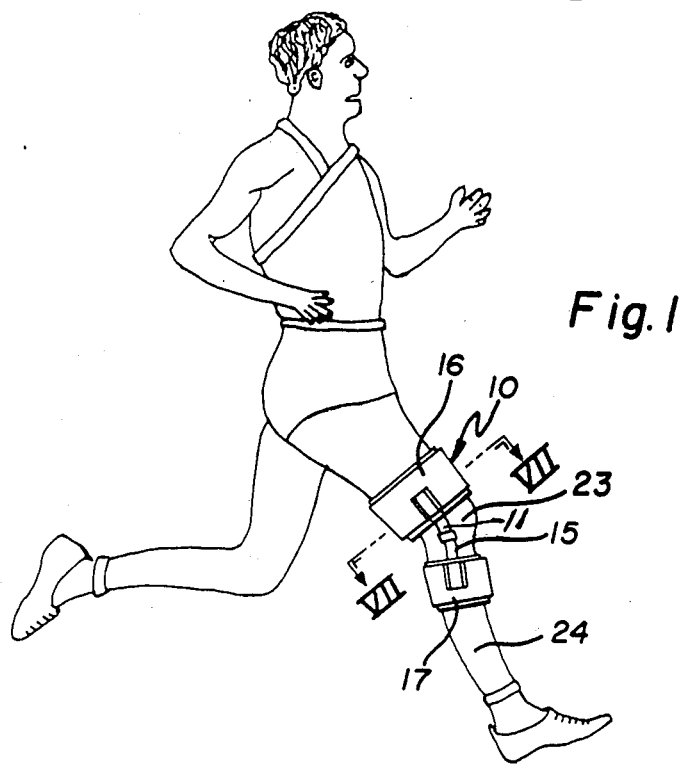
FIG. 1 is a perspective view of an orthopedic brace embodying the principles of the present invention shown in use with an athlete.

Referring first to FIG. 1, which best shows the general features of the invention, it can be seen that the orthopedic brace, indicated generally by the reference numeral 10, consists of an upper cuff 16 located above the knee 23 of a leg 24 of an athlete and a cuff 17 located below the knee. The cuffs are joined by a connector member 15, the connector member being shown in partially-bent condition.

Figure 2:
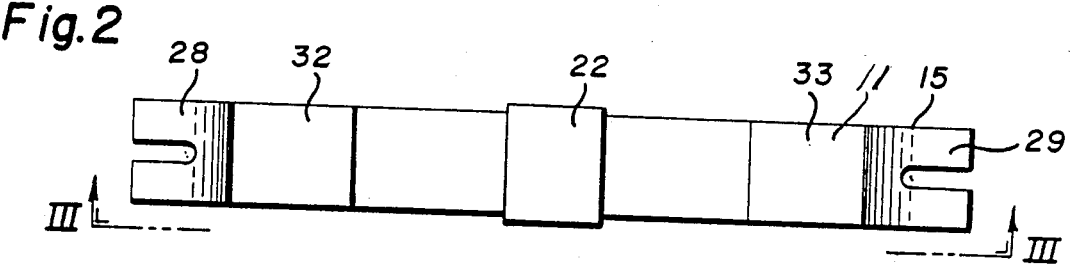
FIG. 2 is a top plan view of a connector member forming part of the invention.
Figure 3:
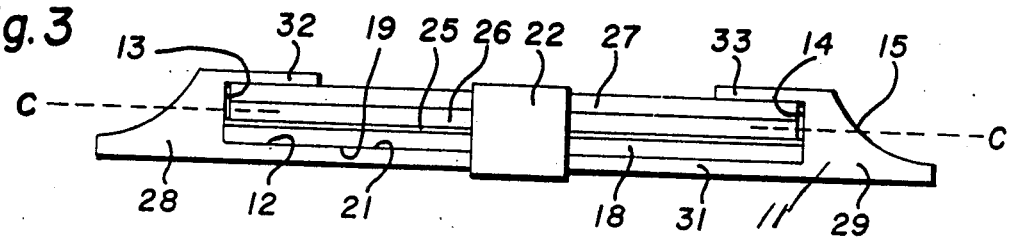
FIG. 3 is a front elevational view of the connector member, taken on the line III—III of FIG. 2.
Figure 4:
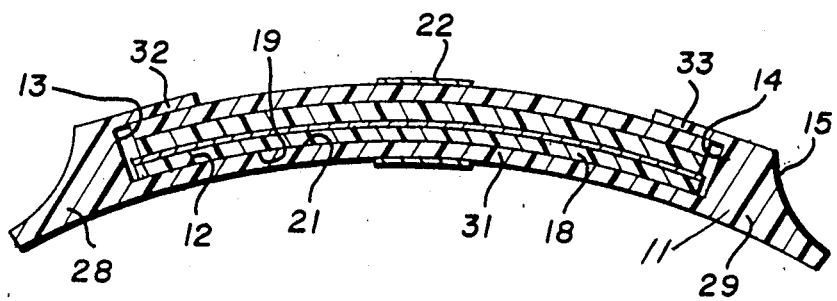
FIG. 4 is a vertical sectional view of the connector member shown in bent condition.
Figure 7:
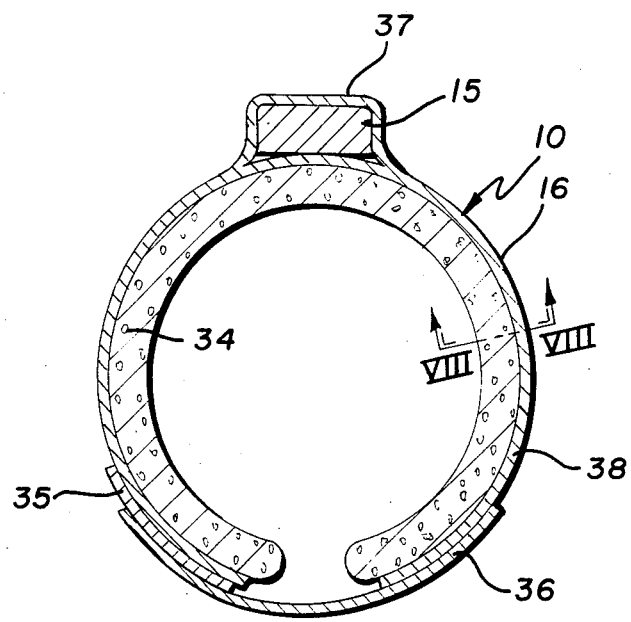
FIG. 7 is a horizontal sectional view of the brace taken on the line VII—VII of FIG. 5.
Figure 5:
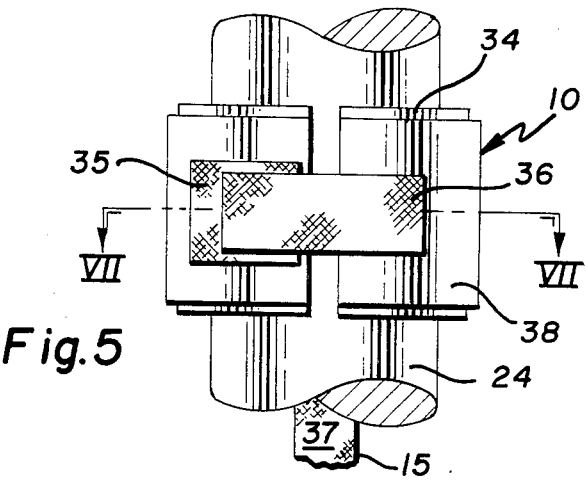
FIG. 5 is a front elevational view of a portion of the brace as viewed from inside the leg or knee.
Figure 6:
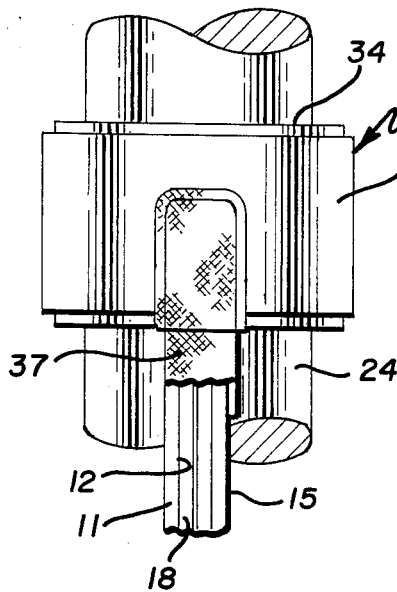
FIG. 6 is a side elevational view of the brace shown from outside the knee.
Figure 8:
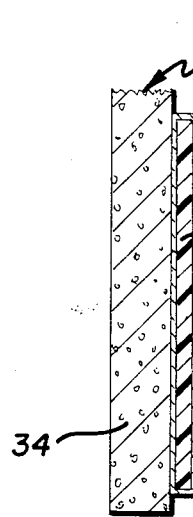
FIG. 8 is a vertical sectional view of the brace taken on the line VIII—VIII of FIG. 7.

Referring next to FIGS. 2, 3, and 4, it can be seen that the connector member 15 includes a main body 11 formed of an elastomer material. The main body is attached at its ends to the cuffs 16 and 17 and is capable of bending in one direction to allow articulation of the limb 24; means is provided for preventing the main body 11 from bending in the other direction or laterally.

The elongated main body 11 is formed with a longitudinal track 12 which has transverse stop surfaces 13 and 14 at either end. The track is located at one side (compression sides) of the neutral plane C—C of the main body. The means for preventing the main body from bending in the other direction or laterally consists of an elongated limiting element 18 lying in the track on the said compression side of the neutral plane. The element is a strip of high-density polyethylene and has its ends lying in contact with the said top surfaces 13 and 14 of the track. The main body 11 and the limiting element 18 are bendable from a first normal position (in which the ends of the limiting elements are close to contact with the stop surfaces) to a second bent position (in which the ends of the limiting element are separated from the stop surfaces, as can be seen in FIG. 4). The limiting element 18 consists of a strip of elastomer plastic located entirely on the compression side of the neutral plane during bending. Other similar strips 25, 26, and 27 lie in the track in contact with the first-mentioned strip. The strip 25 is a metal strip and, in the preferred embodiment, is steel, while the strips 26 and 27 are formed of the same elastomer as the limiting element 18.

The main body is provided with two heads 28 and 29 that are integrally joined by a flexible strip 31. The strip has an inner flat surface 21 which forms part of the track and slidably mates with a similar flat surface 19 on the limiting element 18. The head 28 is provided with the transverse stop surface 13, while the head 29 is provided with the opposed transverse stop surface 14. A projection 32 extends from the head 28, while a similar projection 33 extends from the head 29, the projections extending inwardly toward one another. Each projection has a flat surface that faces is spaced from, and is parallel to the flat surface 21 of the track. The ends of the strips 25, 26, and 27 lie between that last-mentioned flat surface and the said surfaces of the projections. A retainer or clamping means 22 is provided to hold the strips in the track.

Referring to FIGS. 5, 6, 7, and 8, it can be seen that the cuff 16 is similar to the cuff 17 and consists of a U-shaped flexible sleeve 38. A padded lining 34 is fastened to the inside surface of the sleeve and Velcro elements 35 and 36 join the free ends of the sleeve. A cover 37 extends completely around the sleeve 38, around the main body 11 and around the limiting element 18 from one end to the other. This cover 37 is formed from a net-like substance in which reinforcing strands are embedded and which is coated with a polymerized plastic to give it stiffness.

The operation and the advantages of the invention will now be readily understood in view of the above description. As is evident in FIG. 1, the cuff 16 is applied to the limb 24 above the knee 23 while the cuff 17 extends around the limb below the knee. The both cuffs are pulled tightly and held in place by the Velcro elements 35 and 36. The lining 34 is made of foamed plastic and forms a comfortable fit around the limb. The connector 15 extends between the two cuffs. When the user bends his leg at the knee, the cuffs, of course, remain fixed on their respective upper and lower parts of the leg. The connector 15 bends from the normal condition shown in FIG. 3 to the bent condition shown in FIG. 4. In the former condition, the ends of the limiting elements are in contact or close to the surfaces 13 and 14 of the track 12. In the bent condition, however, as is obvious in FIG. 4, the ends of the limiting element 18 are substantially spaced from the stop surfaces 13 and 14.

When the leg is returned to its normal straight position, the connector 15 takes the appearance shown in FIG. 3. If one attempts to bend the connector and the main body 11 in the other direction, the limiting element 18 immediately makes contact with the end surfaces 13 and 14 and becomes, in affect, integral with the main body 11. It then becomes part of the beam and serves to resist bending. A small amount of bending may take place and, when it does, the other strips 26 and 27 then come into contact with the stop surfaces 13 and 14 and resist further bending. The metal strip 25 (which lies between the plastic strips 18 and 26) serves to stiffen the affect of the lowermost strip or limiting element 18. In effect, however, the limiting element consists of all of the strips 18, 25, 26, and 27 and they serve to strengthen the beam and resist bending in the "wrong" direction, including in the lateral directions.

It can be seen, then, that the result of the present invention is a light-weight orthopedic brace which can be inexpensively manufactured. Because it is light-weight (consisting of plastic parts and hardly any metal) it is light enough to permit the user to take part in a sport without tiring easily. Furthermore, in the preferred embodiment there are no connector elements on the facing sides of the two legs, i.e., the insides of the knees. This means that running can take place without interference between the two braces. The connector 15 allows the leg to be bent for running and, yet, it resists motion in the other direction and laterally where damage could be done to the ligaments and muscles. Because the construction is of general applicability to various physical shapes and sizes in the knee area, there is little need to provide a custom-fitting. There would, of course, necessarily be wide differences in size if the brace is to be used with a child rather than a high school student or an adult. The present invention is particularly advantageous as a prophylaxis for the prevention of injury. In this respect, it should be used along with other equipment, particularly in football, where it should be added to the accessories worn by an athlete, as is presently true in the case of the shoulder pads, knee pads, face mask, and the like. The present invention not only protects against a tear of the medial collateral ligament, but also as a protection to the cruciate ligaments, which are the criss-cross band of thick ligaments that lie deep within the knee cavity and which serve to prevent hyperextension of the knee, as well as to prevent instability of the upper femur on the lower tibia platform. The brace is washable and durable, so that it can be used in athletic departments for a long time. It definitely aids in the preventing the consequences of clipping, excessive rotation, and hyperextension of the knee.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. Orthopedic brace for use with a body limb, comprising:
   (a) a first cuff for embracing the limb at one side of a joint,
   (b) a second cuff for embracing the limb at the other side of the joint,
   (c) an elongated connector member, including a main body formed of an elastomer material, the main body being attached at its ends to the cuffs and being capable of bending in one direction only to allow articulation of the limb, and
   (d) means resisting the main body from bending in any other direction.

2. Orthopedic brace as recited in claim 1, wherein each cuff consists of a U-shaped flexible sleeve, a padded lining fastened to the inside surface of the sleeve, and Velcro elements joining the free ends of the sleeve.

3. Orthopedic brace as recited in claim 1, wherein the elongated main body is formed with a neutral plane having a compression side, and a longitudinal track having a transverse stop surface at each end, the track being located on the compression side of the neutral plane of the main body, and wherein the preventing means is an elongated limiting element lying in the track on the compression side of the neutral plane and having ends lying in contact with the said stop surfaces of the track, the main body and the limiting element being bendable from a first normal position in which the ends of the limiting element are close to contact with the stop surfaces to a second bent position in which the ends of the limiting element are separated from the stop surfaces.

4. Orthopedic brace as recited in claim 3, wherein a cover extends completely around the main body, and limiting element from one end to the other.

5. Orthopedic brace as recited in claim 3, wherein the limiting element consists of a strip of elastomer plastic located entirely on the compression side of the neutral plane during bending, and wherein other similar strips lie in the track in contact with the first mentioned strip.

6. Orthopedic brace as recited in claim 5, wherein the main body comprises two heads integrally joined by a flexible strip, the strip having an inner flat surface defining the track and each head having one of the said stop surfaces extending at a right angle to the flat surface, and wherein a projection extends inwardly from each head with a surface lying facing, spaced from, and parallel to the said flat surface, the ends of the strips lying between the said flat surface and the said surfaces of the projections.

7. Orthopedic brace as recited in claim 6, wherein clamping means is provided to hold the strips in the track.

8. Orthopedic brace, comprising:
   (a) an elongated main body having a neutral plane and having a longitudinal track with a transverse stop surface at each end, the track being located at one side of the neutral plane, and
   (b) an elongated limiting element lying in the track on the said one side of the neutral plane and having ends lying adjacent the said stop surfaces of the track, the main body and the limiting element being bendable from a first normal position in which the ends of the limiting element are close to contact with the stop surfaces to a second bent position in which the ends of the limiting element are separated from the stop surfaces, a limb-embracing cuff being attached to each end of the main body.

9. Orthopedic brace, comprising:
   (a) an elongated main body having a neutral plane and having a longitudinal track with a transverse stop surface at each end, the track being located at one side of the neutral plane, and
   (b) an elongated limiting element lying in the track on the said one side of the neutral plane and having ends lying adjacent the said stop surfaces of the track, the main body and the limiting element being bendable from a first normal position in which the ends of the limiting element are close to contact with the stop surfaces to a second bent position in which the ends of the limiting element are separated from the stop surfaces, clamping means being provided midway between the ends of the main body and limiting element to hold them together.

10. Orthopedic brace, comprising:
   (a) an elongated main body formed of an elastomer plastic and formed with a neutral plane and a longitudinal track having a transverse stop surface at each end, the track being located at one side of the neutral plane of the main body, and
   (b) an elongated limiting element lying in the track on the said one side of the neutral plane and having ends lying adjacent the said stop surfaces of the track, the limiting element consisting of strips of elastomer plastic and metal, the main body and the limiting element being bendable in a first direction from a first normal position in which the ends of the limiting element are substantially in contact with the stop surfaces to a second bent position in which the ends of the limiting element are substantially separated from stop surfaces, so that bending in a second opposite direction is terminated by direct contact of the ends of the limiting element with the stop surfaces.

* * * * *